United States Patent

Speck

[11] Patent Number: 6,066,659
[45] Date of Patent: May 23, 2000

[54] USE OF PYRIDOXINE DERIVATIVES IN THE PREVENTION AND TREATMENT OF HYPERLIPIDAEMIA AND ATHEROSCLEROSIS

[75] Inventor: Ulrich Speck, Berlin, Germany

[73] Assignee: Steigerwald Arzneimittelwerk GmbH, Germany

[21] Appl. No.: 08/135,523

[22] Filed: Oct. 12, 1993

Related U.S. Application Data

[60] Division of application No. 07/365,935, Jun. 15, 1989, Pat. No. 5,288,716, which is a continuation-in-part of application No. 07/156,990, Feb. 18, 1988, abandoned.

[30] Foreign Application Priority Data

Feb. 18, 1987 [DE] Germany ............................ 37 05 549

[51] Int. Cl.$^7$ ................................................. A61K 31/435
[52] U.S. Cl. ............................ 514/351; 514/350; 514/824
[58] Field of Search ................................ 514/350, 351, 514/824

[56] References Cited

U.S. PATENT DOCUMENTS 3,426,131 2/1969 Perrault .................................... 514/351

FOREIGN PATENT DOCUMENTS

| 2255883 | 7/1975 | France . |
| 1238473 | 4/1967 | Germany . |
| 3617711 | 12/1987 | Germany . |
| 1360536 | 7/1974 | United Kingdom . |

OTHER PUBLICATIONS

Remington's Pharmaceutical Sci, Oslo et al. ed., (1980) pp. 960–961.
The Merck Index (1983), p. 1151, cit. #7880.
"Drug Absorption, Action and Dispostion", Remington's Pharmaceutical Sciences, 15th Ed., pp. 683–685 (1975).
Merrill et al., "Diseases Associated with Defects in Vitamin B6 Metabolism or Utilization", Ann. Rev. Nutr. 7:137:156, pp. 144.147 (1987).
Chem. Abstracts 98(23):198692 (1983) Kurnuchi.
Chapter 25 "The Biosynthesis of Amino Acids . . . ", In Biochem, 1975, p. 693.
Chem. Abstract 67(17):82109 (1967).
Chem. Abstract 83(17):146652 (1975), Urakami et al.
Chem. Abstract 68(9):39479 (1967) Schorre.
Chem. Abstract 81(17):105304c (1974) Laboratorios.
Rinehart et al., Pathogenesis of Experimental Arteriosclerosis in Pyridoxine Defieiency: A.M.A. Archives of Pathologi, pp. 12, 18. (1980).
Serofotein et al., "Plasma Pyridoxal–5–phosphate Level as Risk Index for Coronary Artery Disease," Atherosclerosis, 55 (1985).
K.H. Bassler, Megavitamin Therpay with Pyridoxine, Internat. J. Vit. Nutr. Res. 58 (1988), pp. 105–118.
Chem. Abstracts 86(3):16550( (1976) Busquets.
Chem. Abstracts 101(25):228946 (1984) Merrill et al.
Chem. Abstracts 109(6):43462 (1987) Elstner.
Chem. Abstracts 98(11):89841u (1983) Casella.

*Primary Examiner*—Raymond Henley, Jr.
*Attorney, Agent, or Firm*—Millen, White, Zelano & Branigan P.C.

[57] ABSTRACT

A method for prevention of atherosclerosis or for treatment of hyperlipidaemia or atherosclerosis comprises administering a compound or a mixture of compounds according to formula (I)

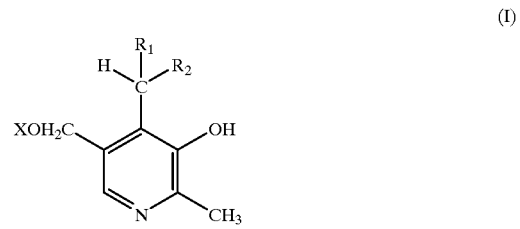

as defined herein.

8 Claims, No Drawings

USE OF PYRIDOXINE DERIVATIVES IN THE PREVENTION AND TREATMENT OF HYPERLIPIDAEMIA AND ATHEROSCLEROSIS

This application is a divisional application of Ser. No. 07/365,935, filed Jun. 15, 1989, now U.S. Pat. No. 5,288,716, which is a continuation-in-part of U.S. Ser. No. 07/156,990 of Feb. 18, 1988 now abandoned, which is incorporated by reference herein.

DESCRIPTION

The invention relates to the use of pyridoxine derivatives in the prevention and treatment of hyperlipidaemia and atherosclerosis. This does not include pyridoxine-5'-phosporic acid ester glutamate and aspartate, which are described in the German Patent DE 24 61 742 C2.

Atherosclerosis is one of the most frequent diseases and causes of death (atherosclerosis of the coronaries) in industrialised countries. Atherosclerosis is usually a slow process comprising complex changes in the structure and function of the blood vessels and ending in clearly visible clinical diseases such as angina pectoris and cardiac infarction through constriction and blockage of coronary vessels, reduced perfusion of the extremities, or brain infarct. The dramatic final stage of the disease is often preceded by long years of severe discomfort and chronic illness. The possibilities of treatment in the advanced stage are very limited, expensive and invasive, e.g. the open-heart operation or amputation of extremeties.

Apart from relatively rare cases of severe hereditary metabolic disturbances, atherosclerosis is to a large extent a disease of civilisation. The risk of atherosclerosis is increased particularly by smoking (nicotine). Other risk factors are e.g. high blood pressure, insufficient physical activity, diabetes mellitus and renal insufficiency. A critically important step in the prevention of atherosclerosis was the recognition of the connection between high blood lipid concentration and increased risk of atherosclerosis including increased risk of death through cardiac infarction (compare Dayton, S., Chapman J., Pearce M., Popiak G., Cholesterol, atherosclerosis, ischaemic heart disease, and stroke, Am.J. Med.72,97 (1970).

Cholesterol-rich food and a high content of animal fat (saturated fatty acids) in food produce an undesirable increase in the content of lipoproteins in the blood, resulting in accelerated development of atherosclerotic lesions.

Since cholesterol is the main substance found in atheromatous plaques, a connection between an elevated cholesterol level and atherosclerosis appears certain.

Lipids, which are insoluble in water, are conveyed in the blood by lipoproteins. A distinction is made between LDL (low-density lipoproteins) and HDL (high-density lipoproteins). LDL-cholesterol is of critical importance in atherogenesis. HDL-cholesterol, on the other hand, conveys excess cholesterol from the periphery back to the liver. Its effect, if any, is protective.

Consequently, the accumulation of cholesterol in the median cells of the aterial walls depends not only on the total concentration of cholesterol in the serum but also on the ratio of LDL to HDL.

Elevated blood lipid concentrations, more particularly elevated LDL concentrations in the blood, increase the deposition of lipids in the arterial walls, which in turn initiates or at any rate intensifies other atherosclerotic changes.

The aim of prevention of atherosclerosis, therefore, has increasingly been to reduce the blood lipid concentrations in general and the LDL cholesterol concentrations in particular.

This aim can be achieved in various ways:

Some cholesterol and saturated fatty acids (likewise undesirable) are supplied in food. Consequently a diet containing little cholesterol or animal fats is the first condition for successful treatment or prevention of atherosclerosis.

However, keeping to a diet is often difficult and also insufficient. The reason is that atherogenic lipids are not only ingested in food but also formed in the body. In order to reduce the concentration of endogenic lipids in the blood also, or at least to reduce their atherogenic effect, a large number of drugs have been developed or recommended for this purpose during the last 20 years.

A simple and relatively harmless method of lowering the cholesterol concentration in the blood is to start with the elimination mechanism thereof. In the liver, cholesterol is converted into bile acids, in which form it enters the intestine. Bile acids are largely reabsorbed and re-used. This enterohepatic circulation can be interrupted if bile acids are retained in the intestine by non-absorbable substances.

Examples of such substances are solid ion-exchangers, certain swelling agents such as guar, and also normal constituents of food such as fibrous materials. These cause the liver to convert more cholesterol into bile acids, thus eliminating it more quickly. A disadvantage of this method of treatment is the extremely high dosage of the preparations in questions (8–24 g/day) and the inconvenience of taking them.

A number of systemically acting "lipid-lowering agents" have also been introduced into treatment, e.g. derivatives of clofibric acid, which inhibit the synthesis of cholesterol in the liver. Owing to the serious side-effects and the required duration of treatment clofibrates are used only for severe disturbances in lipid metabolism (compare Scheffler W. and Schwartzkopff, W., Frequently used lipid-lowering drugs have no guaranteed effect. Artery 8, 120–127 (1980)).

However, other synthetic or even natural drugs (nicotinic acid derivatives) sometimes cause unacceptable side-effects, or the dosage has to be so high, that they place an unacceptable burden on metabolism particularly in the case of long-term treatment of elderly patients or patients with kidney or liver disease.

Some derivatives of pyridoxine phosphate are described in the German Patent DE 24 61 742 C2 as lipid-lowering and antiatherosclerotic active principles. These substances include pyridoxine-5'-phosphoric acid ester glutamate and aspartate. Their effect is attributed to the combination of pyridoxine phosphate and glutamic acid or aspartic acid. In spite of their undoubted efficiency, the known substances also have perceptible disadvantages. They are not strictly natural remedies, their chemistry is badly defined, their stability is questionable, even when very small quantities of moisture are added, and non-existent in vivo, e.g. during absorption, and the doses have to be relatively high. As a result of their instability, the active principles listed in DE 24 61 742 C2 also cannot be administered in the form of infusions or ampoules for drinking or solutions of other kinds. However, ingestion in liquid form is very convenient, particularly for patients who are usually elderly.

Under unfavourable conditions, individual constituents of the substances described in DE 24 61 742 C2 may even have a deleterious effect on the patients. (GB 1,478,560 is equivalent to the mentioned DE.) FR 2,255,883 discloses the combination of clofibrate-type compounds with certain pyridoxine derivatives as a lipid-lowering combination.

Since the patients are usually elderly, suffer from a number of diseases and often have to take lipid-lowering drugs as long as they live, it is desirable to have a natural, well-tolerated drug to be taken in low doses. The drug also needs to have a well-defined chemical composition, to be resistant to external influences and to be substantially unchanged and completely resorbable after oral administrations. The drug should alter the metabolic situation in a manner which, other things being equal, results in reduced deposition of lipids in the arterial wall and thus delays, interrupts or even reverses atherosclerotic changes.

An object of the invention therefore is to provide a novel means for prevention and treatment of hyperlipidaemia and atherosclerosis, which has the aforementioned properties. The substance should also be of use for treating persons who have high blood lipid concentrations even when they are on a diet.

During the search for a suitable active principle it was found that certain derivatives of pyridoxine, more particularly pyridoxal, pyridoxamine and precursors and their metabolites and derivatives, unexpectedly have an aforementioned lipid-lowering, anti-atherosclerotic activity. This was explicitly queried in DE 24 61 742 C2 (column 3, lines 35 ff). On the other hand, pyridoxine, often also called vitamin $B_6$, does not have any strong action in this respect. Pyridoxine was used separately in earlier experiments on animals in conjunction with lipid metabolism (see Frolova, J. A.: Vitamin $B_6$ and lipid metabolism; Vopr. med. Khim. 89, 18. 339–346 (1972)). Its effect, however, is weak. In our experiments, pyridoxine in rats was ineffective at a dose of 79 mg/kg body weight, although a positive control showed the expected effect in the same experiment.

Various pyridoxine derivatives occur in metabolism and to some extent are convertible into one another. These, in addition to pyridoxine itself, include e.g. pyridoxamine, pyridoxal, pyridoxal phosphate and pyridoxic acid. It is generally recognized that the pool of pyridoxal and derivatives thereof is correspondingly increased by oral administration of pyridoxine.

It has now surprisingly been found that oral administration of certain pyridoxine derivatives, more particularly pyridoxal and pyridoxamine or precursors or derivatives thereof, results in a marked reduction in serum lipids, particularly LDL cholesterol, which has such a disastrous effect in atherogenesis. Another effect, apparently independent of the reduction of serum lipids, is the reduced deposition of lipids in the arterial walls. Both actions guarantee an effective preventive and therapeutic treatment of atherosclerosis which on present knowledge, attacks the causes. The treatment is all the more valuable in that it is not offset by any recognizable side-effects. The toxicity of the aforementioned vitamin $B_6$ derivatives is extremely low, and they are therefore extremely well tolerated at the doses used for human treatment. More particularly, there is no toxic effect on the liver, in contrast to most other lipid-lowering agents, which cause a marked increase in the liver weight of experimental animals after only a short period of treatment.

The present invention concerns a compound according to formula I

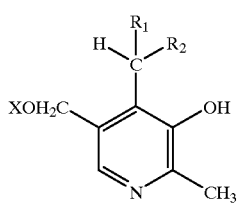

(I)

wherein a) $R_1$ is hydrogen and $R_2$ is

wherein $R_3$ and $R_4$ are independently hydrogen, $C_{1-6}$-alkyl, $C_{2-6}$-alkenyl, (hydroxy or $C_{1-4}$-alkoxy)-$C_{1-6}$-alkyl, $C_{6-14}$-aryl or substituted aryl b) $R_1$ is hydrogen and $R_2$ is

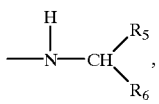

or $R_1$ and $R_2$ together are

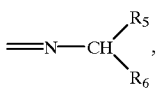

both radicals

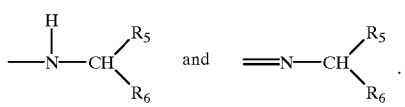

being derived from a natural amino acid, a natural amine, or a respective amide, $R_5$ and $R_6$ being the appropriate radicals, and X is hydrogen,

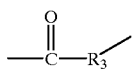

or —$PO_4H_2$, $R_3$ being independently a group defined for $R_3$ above, or salts thereof with the provisos that:

$R_3$ and $R_4$ are not both H when X is H or $PO_4H_2$, when $R_1$ and $R_2$ are =N—$CHR_5R_6$, the latter radical is not derived from glutamic or aspartic acid when X is $PO_4H_2$, and when one of $R_3$ and $R_4$ is H and the other is alkyl, then X is not $PO_4H_2$.

The preferred compounds according to the invention are those compounds wherein $R_1$ and $R_2$ under item 1b) are derived from one of the natural amino acids glycine, alanine, valine, leucine, isoleucine, phenylalanine, serine, threonine, lysine, δ-hydroxylysine, arginine, aspartic acid, asparagine, glutamic acid, glutamine, cysteine, cystine, methionine, tyrosine, thyroxine, proline, hydroxyproline, tryptophan and histidine. Also preffered are those compounds wherein $R_1$ and $R_2$ under item 1b) are derived from one natural amine. "Natural amines" correspond to any amines naturally occurring in mammals. Suitable such amines are disclosed in J. D. Roberts, M. J. Caserio, Basic Principles of Organic Chemistry New York 1965,p.643. Examples are ammonia, methylamine, ethyl-amine, t-butylamine, diethylamine, triethylamine, tri-n-butyl-amine, piperidine, pyridine, cyclohexylamine, aniline, diphenyl-amine, triphenylamine, ethylenediamine, ethanolamine, diethanol-amine, dopamine, sertonine, toluidine, glucosamine, adenine, cytosine, aminopropanediol, serinol, trihydroxybutylamine and p-aminobenzoic acid.

Furthermore, the invention concerns a method for prevention of atherosclerosis and for treatment of hyperlipidaemia and atherosclerosis comprising administering a compound or a mixture of compounds according to formula (I)

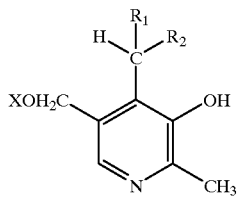
(I)

wherein a) $R_1$ and $R_2$ together are oxygen or b) $R_1$ is hydrogen and $R_2$ is

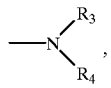

wherein $R_3$ and $R_4$ are independently hydrogen, $C_{1-6}$-alkyl, $C_{2-6}$-alkenyl, (hydroxy or $C_{1-4}$-alkoxy)-$C_{1-6}$-alkyl or $C_{6-14}$-aryl or substituted aryl or c) $R_1$ is hydrogen and $R_2$ is

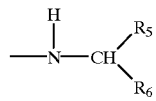

or $R_1$ and $R_2$ together are

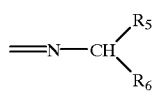

both radicals

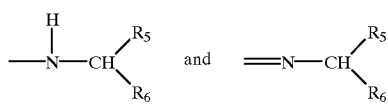

being derived from a natural amino acid, a natural amine, or a respective amide, $R_5$ and $R_6$ being the appropriate radicals, and X is hydrogen,

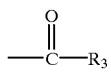

or —$PO_4H_2$, $R_3$ being independently a group defined for $R_3$ above, or a salt thereof with the provisos that:

when (i) $R_1$ and $R_2$ together are oxygen or (ii) one of $R_1$ and $R_2$ is H and the other is $NR_3R_4$ and both $R_3$ and $R_4$ are H or one of $R_3$ and $R_4$ is H and the other is alkyl, then X is not $PO_4H_2$;

when X is H and (i) $R_1$ and $R_2$ are O or (ii) one of $R_1$ and $R_2$ is H and the other is $NR_3R_4$ and both $R_3$ and $R_4$ are H or one of $R_3$ and $R_4$ is H and the other is alkyl, then the resultant compound is not coadministered with clofibric acid or an ester or salt thereof; and that when $R_1$ and $R_2$ are =N—$CHR_5R_6$, the latter radical is not derived from glutamic or aspartic acid when X is $PO_4H_2$.

In other aspects, the foregoing is optionally subjected to the additional provisos that when one of $R^1$ and $R^2$ is H and the other is $NR^3R^4$ and both $R^3$ and $R^4$ are alkyl, then X is $PO_4H_2$; and when X is H and one of $R_1$ and $R_2$ is H and the other is $NR_3R_4$ and both $R_3$ and $R_4$ are alkyl, then the resultant compound is not coadministered with clofibric acid or an ester or salt thereof.

The term "respective amide" refers to amides formed (formally) between the carboxy group of a natural amino acid as defined above and the amino group of a natural amine as defined above according to the following formal scheme:

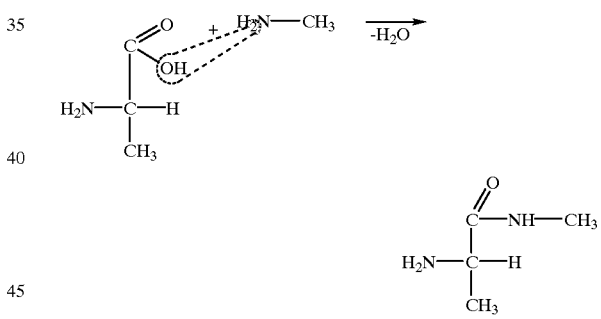

All compounds useful in the method of this application can be made from known or readily preparable starting materials using fully conventional chemical reactions, e.g., by reacting

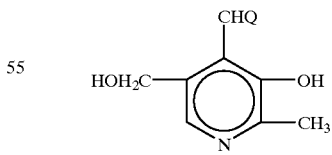

wherein Q is =O(pyridoxal) or H,OH(pyridoxine) with an amine of the formula —$NR_3R_4$ or —NH—$CHR_5R_6$ (utilizing conventional protecting groups where convenient), or for compounds of the structure (c) wherein $R_1$ and $R_2$ are =N—$CHR_5R_6$, by reacting with the corresponding amine under conditions conventional for the formation of Schiff bases. See, for example, the examples below.

Throughout this application, suitable alkyl portions in all corresponding groups mentioned include methyl, ethyl, n-propyl, isopropyl, isobutyl, sec-butyl, n-butyl, t-butyl, and, similarly, the various isomers of pentyl and hexyl. The corresponding alkenyl groups are also included. Suitable aryl groups include phenyl and 1- or 2-naphthyl, each optionally substituted by groups such as $C_{1-4}$-alkyl, $C_{1-4}$-alkylcarbonyloxy, $C_{1-4}$-alkoxycarbonyl, $C_{1-4}$-alkoxy, etc.

In a preferred embodiment the invention concerns a method for prevention of atherosclerosis and for treatment of hyperlipidaemia and atherosclerosis comprising administering pyridoxal, its simple derivatives (e.g., Schiff bases) or pyridoxamine or any mixture thereof. Useful salts of the compounds of this invention are the usual pharmaceutically acceptable salts, e.g., addition salts with acid or bases and are conventionally prepared from conventionally employed acids or bases. Such acids include, for example, inorganic acids, e.g., hydrochloric acid, phosphoric acid, sulfuric acid, hydrobromic acid, hydroiodic acid and phosphorous acid, or organic acids, such as, for example, aliphatic mono- or dicarboxylic acids, phenyl-substitued alkanecarboxylic acids, hydroxyalkanecarboxylic acids or alkenedicarboxylic acids, aromatic acids or aliphatic or aromatic sulfonic acids.

Physiologically acceptable salts of these acids are e.g., the sulfate, pyrosulfate, bisulfate, sulfite, bisulfite, phosphate, monohydrogen phosphate, dihydrogen phosphate, metaphoshate, pyrophosphate, chloride, bromide, iodide, acetate, propionate, decanoate, caprylate, acrylate, formate, isobutyrate, caproate, heptanoate, propiolate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylcetate, phenylpropionate, phenylbutyrate, citrate, lactate, β-hydroxybutyrate, glycolate, malate, tartrate, methanesulfonate, propanesulfonate, naphthalene-1-sulfonate and naphthalene-2-sulfonate. Suitable cations include sodium, potassium, calcium, magnesium and organic amines.

The newly-discovered efficacy of the aforementioned pyridoxine derivatives is all the more surprising in that these compounds, which have a simple structure, were thought to have a low activity and it was expected to obtain effective drugs only by very complex molecules derived from pyridoxal phosphate as described e.g. in the cited DE 24 61 742 C2.

The main substances for clinical use according to the invention are the aforementioned pyridoxine derivates (pyridoxal, pyridoxamine, and simple derivatives thereof) and suitable mixtures thereof. Of course, all other substances are suitable which liberate the aforementioned pyridoxine derivatives in vitro or more particularly in vivo. The pyridoxine derivatives are sufficiently effective per se, but they may also be used in conjunction with other measures for stabilizing lipid metabolism (e.g. diet) or treatment (e.g. bile acid adsorbing agents). A preferred combination is with lipid-lowering agents which act on metabolism at a different point from the aforementioned pyridoxine derivatives. Combinations with drugs for treatment of diseases frequently accompanying atherosclerosis (high blood pressure, diabetes, etc) may also be advantageous. Since the aforementioned pyridoxine or vitamin $B_6$ derivatives are very well tolerated, they are particularly suitable for patients with numerous underlying or accompanying diseases.

On the other hand pyridoxine itself, which is preferably used under the name of vitamin $B_6$, is not suitable.

In practice, treatment is preferably by oral administration of the active principles for a prolonged period. A maximum effect is not expected before two months or longer treatment. Treatment must be continuous, since if the preparations are discontinued the result is a very rapid decrease in the effect, an increase in serum lipids and a worsening of atherosclerosis.

In exceptional cases the active principles used according to the invention may also be administered parenterally, e.g. by intravenous infusion of the aqueous solutions or intramuscular injection thereof.

In oral therapy the daily amount is administered either in one dose or in two or three doses.

The daily amount can be between 20 mg and 1,000 mg, preferably between 50 and 500 mg of the aforementioned vitamin $B_6$ derivatives.

Substances according to the invention, as compared with most other drugs used for prevention and treatment of atherosclerosis, have the important advantage of having a neutral or at least acceptable taste and of being easy to dissolve in water and thus not causing any problems of consistency (no particles, no viscous gel).

Furthermore, the good taste and good solubility of some of the inventive compounds allow to take advantages of the improved bioavailability in case of buccal absorption. In this case the bioavailability is much better in comparison with the metabolic degradation in the intestine and liver.

The very widely-used clofibrates, on the other hand, are nauseously bitter, and substances for adsorbing bile acid are coarse-grained or form voluminous gels.

Since substances according to the invention are soluble in water and chemically stable, elderly patients can also easily take them in the form of a powder or granulate or dissolved in water or a drink. The individual dose may also be administered in the form of a tablet, capsule or coated pill and the dissolution of each of these forms and the liberation of active principle can be delayed and controlled by methods known to skilled persons.

The following table shows the values for the decrease of the concentrations of certain compounds found in hyperlipaemic rabbits after 10 weeks of treatment with pyridoxamine. THe values are mean values of 18 rabbits and measured relative to a basis of non-treated rabbits.

The control group received a diet comprising 2% of cholesterol. In the group under treatment each rabbit received additionally 120 mg pyridoxamine-2 HCl/kg body weight. At the end of the test the aortae of the rabbits from the heart to the bifurcation were prepared and examined:

dry weight—8% lipids (total)—18% cholesterol—27% triglycerides—17% calcium—31%

Thus, pyridoxamine·2 HCl after a treatment of only 10 weeks causes a substantial decrease of those changes that are characteristic for atherosclerosis: thickening of the walls (measured as dry weight), lipid- and calcium uptake.

Thus, generically this invention relates to a method for prevention of atherosclerosis or for treatment of hyperlipidaemia or atherosclerosis comprising administering a compound or a mixture of compounds according to formula (I)

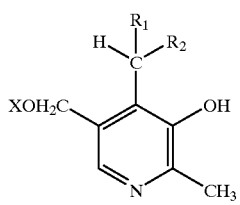

(I)

wherein in formula (I), —CHR₁R₂ is a group linked to the pyridoxine ring by —CH₂—N= or by —CH=N—.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, cited above, and of corresponding German application P 37 05 549.6, are hereby incorporated by reference.

EXAMPLES

1. Capsules a) 500 g of pyridoxal·HCl or pyridoxamine·2 HCl were homogeneously mixed with 1,000 g lactose and 150 mg portions thereof were poured into gelatin capsules. The capsule halves were stuck or welded together. The capsule is taken three times a day at meals.

b) 300 mg pyridoxal·HCl or pyridoxamine·2 HCl were welded in gelatin capsules. To be taken once every evening.

2. Tablets for buccal application 1,000 g pyridoxal phosphate magnesium salt were homogeneously mixed with 3,000 g lactose and 15 g magnesium stearate, granulated and moulded into tablets each weighing 301.5 mg. One tablet to slowly dissolve in the mouth every morning and evening.

3. Tablets resistant to gastric juice 1,000 g pyridoxal·HCl or pyridoxamine·2 HCl were uniformly mixed with 2,000 g tablettose (granulated lactose) and 15 g magnesium stearate, granulated and moulded into approximately round tablets weighing 150 and 75 mg.20 coatings of cellulose acetate succinate (9 parts) dimethyl phthalate (3.4 parts), acetic acid ester (84.4 parts) and acetone (84.4 parts) were applied, using talcum as a dispersion agent. One or two tablets to be taken three times a day before meals.

4. Effervescent tablets 500 g pyridoxal phosphate, 600 g citric acid and 280 g sodium carbonate were mixed with 2,000 g lactose and moulded when dry into 338 mg units. One or two tablets dissolved in a little water to be taken at meals.

5. Granulate 1,000 g pyridoxal·HCl were granulated with 1,000 g citric acid and 8,000 g lactose, after which the granulate was screened to obtain a uniform particle size of about 1 mm. The granulate was thoroughly dried and welded in aluminium foil. The individual dose per bag was 500 mg or 1 g. The contents of the bag is dissolved in water or fruit juice when taken. To increase the effect, a conventional commercial guar preparation or other lipid-lowering drug can be added, preferably a product in which the active principle is not absorbable or has a supplementary mechanism of action, the drug being optionally dissolved when taken.

Preparation of Compounds According to the Invention

Example 1

N-ethylpyridoxamine

Method A

To 2 parts of ethylamine 1 part of pyridoxal and 5 parts of dioxane/tetrahydrofuran were added under $N_2$ as protecting gas. When the reaction came to the end the temperature was increased to 50° C. 0.1 parts of 10% palladium charcoal were mixed to the slightly yellow solution. Hydrogenation was performed in an autoclave applying 3 bar pressure until 1 equivalent hydrogen was taken up. After filtration the reaction mixture was poured into water and stirred. The precipitate was separated by filtration and dried. The crude product was purified by chromatography (silica gel column, dioxane/water), yield: 80%, sintering starts at 170° C., afterwards decomposition.

Method B

One part of pyridoxal dissolved in ethanol was added under stirring to 1 part ethylamine and 0.1 part of a catalyst (e.g. 10% suspension of palladium-charcoal). The mixture was treated in an autoclave until 1 equivalent of hydrogen was taken up. After the usual work-up N-ethylpyridoxamine was obtained as described in method A; yield: 90%.

Examples 2a, 2b, 2c, 2d

As described for example 1 method A or B pyridoxal was treated with a) n-butylamine
b) 3-oxabutylamine
c) benzyl-O-ethylamine
d) 2-0-acetyl-4-aminobenzoic acid methylester 2a) N-butylpyridoxamine was abtained in a yield of 90% amorphous powder, sintering starts at 150° C.; afterwards slow decomposition;

2b) N-[3-oxa-butyl]-pyridoxamine, yield 70%, amorphous powder, melting starts at 180° C.;

2c) N-[2-hydroxyethyl]-pyridoxamine, sintering starts at 160° C. with slow decomposition;

2d) N-[3-acetoxy-4-methoxy carbonylphenyl]-pyridoxamine, sintering at 205° C.

Example 3

Pyridoxal-5-0-enanthoyl

A solution of 1 part of pyridoxal in dioxane was added to catalytical amounts of dimethylamino-pyridine and 2 parts of enanthic acid anhydride. The mixture was warmed up to 60° C. and stirred for 3 hours. The reaction mixture was poured into water and filtered; the precipitate was collected and chloroform was added. The mixture was repeatedly extracted by a solution of bicarbonate. After drying the solvent was distilled off, and the residue was recrystallized from tetrahydrofuran.

Examples 3a, 3b

Similar to example 3 pyridoxal was treated with 3a) methoxy acetic acid anhydrate,
3b) benzoic acid anhydrate,
to obtain the respective 5-0-acyl-products, which were purified by column-chromatography.

Preferably they were reacted according to example 1 and 2 to yield the respective 5-0-acyl-3-N-alkyl or aryl compounds.

Example 4

5-0-acetyl-N-ethylpyridoxamine 5-0-acetyl-pyridoxal was obtained according to example 2. It was reacted with ethylamine using method B. A pale yellow powder was obtained; yield 30%.

Example 5

Schiff Bases of Pyridoxal and Amines or Aminoacids

Method C 1 part of pyridoxal and 1 part of glutamic acid and 1 part of $MgCO_3$ were dissolved or suspended in 50 parts of water. The mixture was warmed to 50° C. and stirred until all ingredients were fully dissolved. The solvent was distilled off under reduced pressure. The Schiff base of pyridoxal glutamic acid was obtained as brownish-yellow powder; sintering and decomposition starts at 200° C.

5a) Method D 1 part of L-arginine was dissolved in 50 parts of 0.1 M sulfuric acid and then treated with 1 part of pyridoxal·HCl The solution was kept for 1 day at 40° C. Ammonia was added to adjust the pH value to 9. Water was partly evaporated at reduced pressure; the yellow precipitate was washed with ice-cold water.

Yield: 20% of Schiff base of pyridoxal arginine.

Examples 5b, c

5b) Schiff base of pyridoxal-5-phosphate phenylalanine was obtained according to method C using pyridoxal-5-phosphate and phenylalanine in equimolar amounts and 2 parts of $MgCO_3$.

5c) Schiff base of pyridoxal tryptamine was obtained according to method D yielding in 30%, of powder; meeting point and decomposition 255° C.

Examples according to 5a, b or c may be hydrogenated as described in method A.

Experimental data:

1. Effect of vitamin $B_6$ and a derivative thereof on serum lipids in rats after 12 weeks of treatment.

Group A=rats fed with normal diet without cholesterol

Group B=rats fed with a diet containing 2.5% cholesterol plus 0.25% cholic acid

Group C=as group (B) plus 79 mg pyridoxine/kg bodyweight

Group D=as group (B) plus an equimolar (to pyridoxine) dose of a pyridoxamine derivative 20 animals per group; mean ± SD; difference to group B in %

|  | Group A | Group B | Group C | Group D |
|---|---|---|---|---|
| Total serum cholesterol | 72 ± 23 | 213 ± 91 | 204 ± 79 −4% | 165 ± 54 −23% |
| LDL + VLDL-Cholesterol | 11 ± 5 | 166 ± 61 | 150 ± 74 −10% | 113 ± 61 −32% |

2. Effect of vitamin $B_6$ and the equimolar dose of a derivative thereof on the calcium and lipid content of the aorta of rabbits after 10 weeks of treatment as compared to a control group fed with a diet containing 2% cholesterol

|  | % difference to control ||
|---|---|---|
|  | Group A pyridoxamine · 2HCl 78 mg/kg bodyweight | Group B pyridoxine · HCl 62 mg/kg bodyweight |
| dry weight | −7% | −1% |
| total lipids | −15% | −3% |
| cholesterol | −21% | −2% |
| triglycerides | −15% | +6% |
| calcium | −24% | +21% |

3. Tolerance of vitamin $B_6$ and two derivatives in mice after a single oral dose of 5 g

|  | % death |
|---|---|
| Pyridoxine | 30 |
| Pyridoxal | 100 |
| Pyridoxamine | 0 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for prevention of atherosclerosis and/or for treatment of hyperlipidemia or atherosclerosis comprising administering to a host in need thereof an effective amount of a compound or a mixture of compounds according to formula (I)

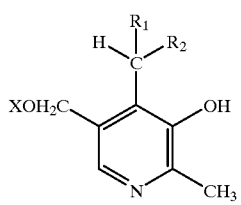

(I)

wherein $R_1$ and $R_2$ together are oxygen and X is hydrogen or

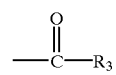

, $R_3$ being independently, hydrogen, $C_{1-6}$-alkyl, $C_{2-6}$-alkenyl, (hydroxy or $C_{1-4}$-alkoxy)-$C_{1-6}$-alkyl or $C_{6-14}$-aryl or substituted aryl, or a pharmaceutically acceptable salt of said compound; with the proviso that:

when X is H, then the resultant compounds is not coadministered with clofibric acid or an ester or salt thereof.

2. A method according to claim 1, wherein a physiologically acceptable pharmaceutical excipient and/or adjuvant is copresent with a compound or a mixture of compounds according to formula I in a suitable dosage form.

3. A method according to claim 1, wherein a compound or a mixture of compounds according to formula I is administered in solid form or as an aqueous solution together with a pharmaceutically acceptable excipient and/or adjuvant.

4. A method according to claim 1, wherein the compound or a mixture of compounds according to formula I is formulated with a physiologically acceptable pharmaceutical carrier and/or adjuvant for buccal application.

5. A method according to claim 1, wherein the compound or a mixture of compounds according to formula I is formulated with a physiologically acceptable pharmaceutical carrier and/or adjuvant in form of a pill covered by a coating which is insoluble at low pH value in the stomach and dissolves only after transfer to the duodenum.

6. A method of claim 1 for prevention of atherosclerosis.

7. A method of claim 1 for treatment of hyperlipidaemia.

8. A method of claim 1 for treatment of atherosclerosis.

* * * * *